(12) United States Patent
Subramaniyam

(10) Patent No.: US 9,234,057 B2
(45) Date of Patent: *Jan. 12, 2016

(54) COMPOSITION OF QUINONE METHIDE DERIVATIVES AND AMINES FOR CONTROL AND INHIBITION OF POLYMERIZATION OF MONOMERS, AND METHOD OF PREPARATION AND USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/423,218

(22) PCT Filed: Aug. 21, 2013

(86) PCT No.: PCT/IB2013/056787
§ 371 (c)(1),
(2) Date: Feb. 23, 2015

(87) PCT Pub. No.: WO2014/030131
PCT Pub. Date: Feb. 27, 2014

(65) Prior Publication Data
US 2015/0225495 A1    Aug. 13, 2015

(30) Foreign Application Priority Data
Aug. 24, 2012   (IN) .................. 2465/MUM/2012

(51) Int. Cl.
| C08F 2/00 | (2006.01) |
| C09K 15/22 | (2006.01) |
| C08F 112/08 | (2006.01) |
| C07C 7/20 | (2006.01) |
| C08F 2/38 | (2006.01) |
| C08F 2/40 | (2006.01) |
| C09K 15/24 | (2006.01) |

(52) U.S. Cl.
CPC ............... *C08F 112/08* (2013.01); *C07C 7/20* (2013.01); *C08F 2/38* (2013.01); *C08F 2/40* (2013.01); *C09K 15/24* (2013.01)

(58) Field of Classification Search
CPC ............ C07C 7/20; C07C 15/46; C08F 2/38; C08F 2/40; C08F 112/08; C08F 12/08; C08K 15/24

USPC .......................................... 526/208; 252/403
See application file for complete search history.

(56) References Cited

U.S. PATENT DOCUMENTS

| 5,583,247 A | 12/1996 | Nesvadba et al. |
| 5,670,692 A | 9/1997 | Nesvadba et al. |
| 6,024,894 A | 2/2000 | Arhancet |
| 7,651,635 B1 | 1/2010 | Lewis |
| 2004/0034247 A1* | 2/2004 | Eldin ..................... C07B 63/04 560/4 |

FOREIGN PATENT DOCUMENTS

| IN | 2465MUM2012 | 8/2012 |
| WO | 2013054353 A1 | 4/2013 |
| WO | 2013054353 A4 | 4/2013 |
| WO | 2013102930 A1 | 7/2013 |
| WO | 2013102930 A8 | 7/2013 |
| WO | 2014030131 A1 | 2/2014 |

OTHER PUBLICATIONS

Foreign communication from the priority application—International Preliminary Report on Patentability, PCT/IB2013/056787, Oct. 2, 2014, 23 pages.
Foreign communication from the priority application—International Search Report and Written Opinion, PCT/IB2013/056787, Oct. 18, 2013, 4 pages.
Foreign communication from the priority application—Second Written Opinion, PCT/IB2013/056787, Jun. 24, 2014, 5 pages.

* cited by examiner

*Primary Examiner* — William Cheung
(74) *Attorney, Agent, or Firm* — Conley Rose, P.C.; Rodney B. Carroll

(57) ABSTRACT

The present invention relates to additive composition for control and inhibition of polymerization of monomers including styrene, wherein the composition consists of:
(a) one or more of quinone methide derivatives; and
CHARACTERIZED IN THAT the composition further comprises:
(b) one or more of tertiary amines,
wherein said tertiary amine is selected from a group consisting of:
(i) tri isopropanol amine (TIPA),
(ii) N,N,N',N'-Tetrakis(2-hydroxyethyl)ethylene-diamine) (THEED), and
(iii) mixture thereof.
In one embodiment, the present invention relates to method of preparation thereof and uses thereof, and a method for controlling and inhibiting polymerization of monomers including styrene.

23 Claims, No Drawings

COMPOSITION OF QUINONE METHIDE DERIVATIVES AND AMINES FOR CONTROL AND INHIBITION OF POLYMERIZATION OF MONOMERS, AND METHOD OF PREPARATION AND USE THEREOF

CROSS-REFERENCE TO RELATED APPLICATIONS

This application is a filing under 35 U.S.C. 371 of International Application No. PCT/IB2013/056787 filed Aug. 21, 2013, entitled "Composition of Quinone Methide Derivatives and Amines for Control and Inhibition of Polymerization of Monomers, and Method of Preparation and Use Thereof," which claims priority to Indian Patent Application No. 2465/MUM/2012 filed Aug. 24, 2012, which applications are incorporated by reference herein in their entirety.

FIELD OF THE INVENTION

The present invention relates to additive composition comprising quinone methide (QM) derivatives and amines for control and inhibition of polymerization of aromatic vinyl monomers (may be referred to as 'monomer' or 'monomers' or 'monomer stream' or 'monomers stream'), particularly of styrene.

In one embodiment, the present invention relates to a method of preparation of additive composition comprising quinone methide (QM) derivatives and amines for control and inhibition of polymerization of monomers, particularly of styrene.

In another embodiment, the present invention relates to a method for controlling and inhibition of polymerization of aromatic vinyl monomers including styrene by employing the additive composition comprising quinone methide (QM) derivatives and amines.

In still another embodiment, the present invention relates to use of or method of using the additive composition comprising quinone methide (QM) derivatives and amines to control and inhibit polymerization of monomers, particularly of styrene.

BACKGROUND OF THE INVENTION

The polymerization of monomers, particularly of styrene during processing is a matter of concern, because it causes formation of unwanted polymers and results in loss of yield of end product and makes the process un-economical.

In the prior art use of inhibitors and retarders, and combination thereof to overcome problem of polymerization of styrene has been reported.

The problem of using the inhibitors alone is that these are to be added continuously or at regular interval, because once they are consumed, the polymerization will re-start.

The problem of using the retarders alone is that these are not very effective to reduce polymerization of styrene to a level of substantial inhibition or to the commercially acceptable level of inhibition.

The prior art discloses use of some of quinone methide (QM) derivatives including 4-benzylidene, 2,6 di tert butyl cyclohexa-2,5 dienone as polymerization inhibitor. However, the inventor has found [refer to examples—Table 1] that main problem of using the quinone methide (QM) is that it has to be used in higher amounts to achieve commercially acceptable level of inhibition, and such higher amount not only results in increase of cost of process, but also results in formation of undesired products due to unstable nature of quinone methide.

The prior art also proposes quinone methide based composition comprising quinone methide (QM) derivatives including 4-benzylidene, 2,6 di tert butyl cyclohexa-2,5 dienone and 4HT (4 hydroxy tempo 2,2,6,6-tetramethyl-,1-oxide) as styrene polymerization inhibitor. However, the inventor has found that main problem of using this known composition of quinone methide is that even at higher amounts the problem of polymerization is not resolved to commercially acceptable level.

The prior art [U.S. Pat. No. 7,651,635] discloses use of combination of an inhibitor and a retarder, wherein the inhibitor is "polymerization inhibitor" consisting of alkylhydroxylamine and retarder is 7-substituted quinone methide (substituted QM). The main problem of this composition is that it employs inhibitor, which are consumed continuously and get gradually depleted, and hence, the inhibitor has to be added continuously or intermittently or at least it has to be ensured that an appropriate amount of the inhibitor is maintained in the system [Col. 4, lines 7-13 of US '635].

The co-pending International (PCT) patent application no. PCT/IN2012/000553 discloses an additive composition comprising quinone methide (QM), and amine or oxide treated derivative of amine.

The another co-pending International (PCT) patent application no. PCT/IN2012/000839 discloses an additive composition comprising:

(A) one or more of the quinone methide or derivatives thereof, (B) one or more of nitroxides (i.e. nitroxyl) compounds, and characterized in that the said composition further comprises:

(C) one or more of aliphatic tertiary amines or mixture thereof.

Need of the Invention

Therefore, there is still a need of additive composition which is not only suitable for substantial control and inhibition of polymerization of monomers including styrene, but is also required in very low dosage.

There is also a need to have a method of preparation of additive composition suitable for substantial control and inhibition of polymerization of monomers including styrene, particularly at a very low dosage.

There is also a need to have a method for controlling and inhibition of polymerization of monomers including styrene by employing the additive composition comprising quinone methide (QM) derivatives and amines, which is also required at lower dosage.

There is further a need to have a use of or method of using additive composition to substantially control and inhibit polymerization of monomers including styrene, particularly at a very low dosage.

Problem to be Solved by the Invention

Therefore, the present invention aims at providing a solution to above-described existing industrial problems by providing additive composition which is not only suitable for substantial control and inhibition of polymerization of monomers including styrene, but is also required in very low dosage.

The present invention also aims at providing a solution to above-described existing industrial problems by providing a method of preparation of additive composition suitable for substantial control and inhibition of polymerization of monomers including styrene, particularly at a very low dosage.

The present invention also aims at providing a solution to above-described existing industrial problems by providing a method for controlling and inhibition of polymerization of monomers including styrene by employing the additive composition comprising quinone methide (QM) derivatives and amines, which is also required at a lower dosage.

The present invention also aims at providing a solution to above-described existing industrial problems by providing a use of or method of using additive composition to substantially control and inhibit polymerization of monomers including styrene, particularly at a very low dosage.

Objects of the Invention

Accordingly, main object of the present invention is to provide additive composition which is not only suitable for substantial control and inhibition of polymerization of monomers including styrene, but is also required in a lower dosage as compared to dosage of the prior art additives for achieving the same or better level of inhibition of polymerization of monomers including styrene.

Another object of the present invention is to provide a method of preparation of the additive composition suitable for substantial control and inhibition of polymerization of monomers including styrene, particularly at a lower dosage as compared to dosage of the prior art additives for achieving the same or better level of inhibition of polymerization of monomers including styrene.

Still another object of the present invention is to provide a method for controlling and inhibition of polymerization of monomers including styrene by employing the additive composition comprising quinone methide (QM) derivatives and amines, which is to be employed at a lower dosage as compared to dosage of the prior art additives for achieving the same or better level of inhibition of polymerization of monomers including styrene.

Yet another object of the present invention is to provide use of or a method of using the additive composition to substantially control and inhibit polymerization of monomers including styrene, particularly at a lower dosage as compared to dosage of the prior art additives for achieving the same or better level of inhibition of polymerization of monomers including styrene.

The present invention aims at providing additive composition which can give commercially acceptable level of inhibition of polymerization, that is, can reduce the polymerization of monomer including styrene even at lower active dosage as compared to dosage of the prior art additives for achieving the same or better level of inhibition of polymerization of monomers including styrene.

The present invention also aims at providing additive composition wherein amount of quinone methide (QM) derivative is substantially reduced in the additive composition, and therefore, the composition of present invention is comparatively economical. The quinone methide (QM) derivatives are expensive and not easily available.

Other objects and advantages of the present invention will become more apparent from the following description when read in conjunction with examples, which are not intended to limit scope of the present invention.

DETAILED DESCRIPTION OF THE INVENTION

With aim to overcome above-described problems of the prior art and to achieve above-described objects of the invention, the inventor has found that when a composition comprising:
(a) one or more of quinone methide (QM) derivatives; and
(b) one or more of preferred polymerization non-inhibiting amines
of the present invention is employed, the polymerization of monomers including styrene, surprisingly and unexpectedly, is substantially controlled and inhibited to the commercially acceptable level (as defined herein), that is, the performance of the additive consisting only of quinone methide (QM) derivative alone, or only of preferred polymerization non-inhibiting amine alone is substantially improved when a composition comprising the combination of (a) one or more of the QM derivatives and (b) one or more of the preferred polymerization non-inhibiting amines is used, which confirms surprising, unexpected and synergistic effects of the presently provided composition. The inventor has found that the polymerization non-inhibiting amines, which have been found to have above-discussed surprising, unexpected and synergistic effects are tertiary amines, and as per inventor's findings the tertiary amine may be selected from a group consisting of:
(i) tri isopropanol amine (TIPA),
(ii) N,N,N',N'-Tetrakis(2-hydroxyethyl)ethylene-diamine) (THEED), and
(iii) mixture thereof.

The inventor has further found that it is further surprising and unexpected that composition comprising the quinone methide (QM) derivative and a polymerization non-inhibiting amine, particularly a tertiary amine other than above-said tertiary amines (i), (ii), and (iii) may have effect in controlling and inhibiting the polymerization of monomers including styrene, and performance of that composition may be comparatively improved than that of performance of the additive composition consisting only of that tertiary amine, however, the performance of that composition is comparatively poorer than that of the performance of the additive composition consisting only of QM derivative alone, which also confirms surprising, unexpected and synergistic effects of the presently provided compositions.

Accordingly, in one embodiment, the present invention relates to additive composition for controlling and inhibiting polymerization of monomers including styrene, wherein the composition consists of:
(a) one or more of quinone methide derivatives; and
CHARACTERIZED IN THAT the composition further comprises:
(b) one or more of polymerization non-inhibiting amines, which are tertiary amines.

The term "polymerization non-inhibitor amine" means, contrary to disclosure and teachings of prior art, the amine per se is not capable of inhibiting polymerization of styrene to the (commercially) acceptable level as discussed above. It has been found that the "polymerization non-inhibiting amines" of the present invention and the comparative amines result in substantially high polymerization of about 14.64% to 17.80% polymerization of styrene as against 19.66% polymerization of styrene for blank example run without amine (see Table 2), and therefore, the "tertiary amines" of the present invention and the comparative amines are named as "polymerization non-inhibitor amines".

In accordance with one of the preferred embodiments of the present invention, the aliphatic tertiary amine of the present invention contains one or more hydroxyl groups, and wherein said one or more hydroxyl groups are in the alkyl chain of said tertiary amine.

In accordance with the present invention, when said aliphatic tertiary amine contains three hydroxyl groups, it is tri-isopropanol amine (TIPA) having following structural Formula-I, and when said aliphatic tertiary amine contains four hydroxyl groups, it is N,N,N',N'-Tetrakis(2-hydroxyethyl)ethylene-diamine) (THEED) having following structural formula-II.

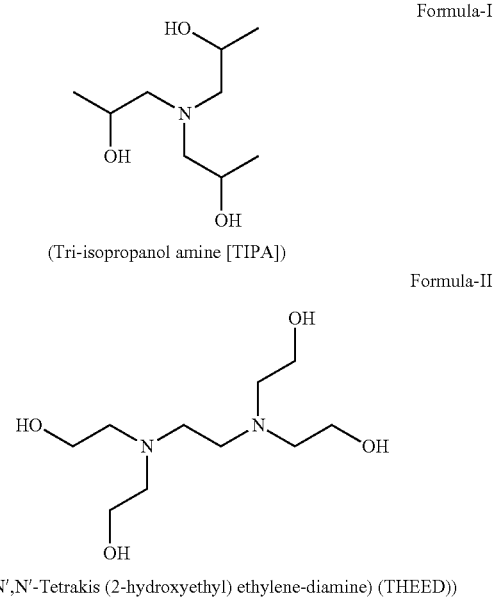

Formula-I (Tri-isopropanol amine [TIPA])

Formula-II (N,N,N',N'-Tetrakis (2-hydroxyethyl) ethylene-diamine) (THEED))

Accordingly, in another embodiment, the present invention relates to additive composition for controlling and inhibition of polymerization of aromatic vinyl monomers including styrene, wherein the composition consists of:
(a) one or more of quinone methide derivatives; and
CHARACTERIZED IN THAT the composition further comprises:
(b) one or more of tertiary amines,
wherein said tertiary amine is selected from a group consisting of:
(i) tri isopropanol amine (TIPA),
(ii) N,N,N',N'-Tetrakis(2-hydroxyethyl)ethylene-diamine) (THEED), and
(iii) mixture thereof.

Accordingly, in further embodiment, the present invention relates to additive composition for control and inhibition of polymerization of styrene, wherein the composition consists of:
(a) one or more of quinone methide derivatives; and
CHARACTERIZED IN THAT the composition further comprises:
(b) one or more of tertiary amines,
wherein said tertiary amine is tri isopropanol amine (TIPA).

Accordingly, in still another embodiment, the present invention relates to additive composition for control and inhibition of polymerization of styrene, wherein the composition consists of:

(a) one or more of quinone methide derivatives; and
CHARACTERIZED IN THAT the composition further comprises:
(b) one or more of tertiary amines,
wherein said tertiary amine is N,N,N',N'-Tetrakis(2-hydroxyethyl)ethylene-diamine) (THEED).

Accordingly, in yet another embodiment, the present invention relates to additive composition for control and inhibition of polymerization of styrene, wherein the composition consists of:
(a) one or more of quinone methide derivatives; and
CHARACTERIZED IN THAT the composition further comprises:
(b) one or more of tertiary amines,
wherein said tertiary amine is combination of:
(i) tri isopropanol amine (TIPA), and
(ii) N,N,N',N'-Tetrakis(2-hydroxyethyl)ethylene-diamine) (THEED).

In accordance with one of the embodiments of the present invention, the quinone methide derivative is selected from a group comprising:
i) alkyl-(3,5-di-tert-butyl-4-oxocyclohexane-2,5-dienylidene)-cyano derivative of quinone methide;
ii) alkyl-(3,5-di-tert-butyl-4-oxocyclohexane-2,5-dienylidene)-acid derivative of quinone methide;
iii) alkyl-(3,5-di-tert-butyl-4-oxocyclohexane-2,5-dienylidene)-ester derivative of quinone methide; and
iv) combination thereof.

In accordance with one of the preferred embodiments of the present invention, the quinone methide derivative is alkyl-(3,5-di-tert-butyl-4-oxocyclohexane-2,5-dienylidene)-ester derivative of quinone methide.

In accordance with one of the preferred embodiments of the present invention, the alkyl group is selected from a group comprising methyl-group, ethyl-group and propyl-group.

In accordance with one of the preferred embodiments of the present invention, the quinone methide derivative does not include 7-aryl quinone methide derivatives.

In accordance with one of the embodiments of the present invention, the quinone methide derivative and the tertiary amine are present in the present composition in a weight percent ratio, wherein the weight percent ratio is selected from the group comprising the weight percent ratio of quinone methide derivative:tertiary amine varying from
i. about 99.99:0.01 to about 40:60,
ii. about 99.9:0.1 to about 50:50,
iii. about 99:1 to about 60:40,
iv. about 95:5 to about 70:30, and
v. about 90:10 to about 85:15.

In accordance with one of the preferred embodiments of the present invention, the polymerization of monomers including styrene, surprisingly and unexpectedly, reduces from about 5.90% when about 100 ppm of quinone methide ester derivative alone is used to about 4.3% when composition of the present invention consisting of about 100 ppm of quinone methide ester derivative and about 1 ppm of TIPA is used, i.e. when QM ester derivative and the tertiary amine are taken in a weight percent ratio of 99.01:0.99, which further reduces to 1.46% when about 100 ppm of quinone methide ester derivative and about 100 ppm of TIPA is used, i.e. when QM ester derivative and the tertiary amine are taken in a weight percent ratio of 1:1.

In accordance with another one of the preferred embodiments of the present invention, the polymerization of monomers including styrene, surprisingly and unexpectedly, substantially reduces from about 1.99% when about 150 ppm of quinone methide ester derivative alone is used to about 0.89% when composition of the present invention consisting of about 150 ppm of quinone methide ester derivative and about 0.75 ppm of TIPA is used, i.e. when QM ester derivative and the tertiary amine are taken in a weight percent ratio of 99.05: 0.50, which further reduces to 0.08% when about 150 ppm of quinone methide ester derivative and about 150 ppm of TIPA is used, i.e. when QM ester derivative and the tertiary amine are taken in a weight percent ratio of 1:1.

In accordance with still another one of the preferred embodiments of the present invention, the polymerization of monomers including styrene, surprisingly and unexpectedly, reduces from about 0.90% when about 200 ppm of quinone methide ester derivative alone is used to about 0.78% when composition of the present invention consisting of about 200 ppm of quinone methide ester derivative and about 0.10 ppm of TIPA is used, i.e. when QM ester derivative and the tertiary amine are taken in a weight percent ratio of 99.95:0.05, which further reduces to 0.55% when about 200 ppm of quinone methide ester derivative and about 0.5 ppm of TIPA is used, i.e. when QM ester derivative and the tertiary amine are taken in a weight percent ratio of 99.75:0.25, which further substantially reduces to 0.07% when about 200 ppm of quinone methide ester derivative and about 30 ppm of TIPA is used, i.e. when QM ester derivative and the tertiary amine are taken in a weight percent ratio of 86.96:13.04, which further substantially reduces to 0% when about 200 ppm of quinone methide ester derivative and about 40 ppm of TIPA is used, i.e. when QM ester derivative and the tertiary amine are taken in a weight percent ratio of 83.33:16.67.

In accordance with yet another one of the preferred embodiments of the present invention, the polymerization of monomers including styrene, surprisingly and unexpectedly, reduces from about 0.23% when about 300 ppm of quinone methide ester derivative alone is used to about 0.15% when composition of the present invention consisting of about 300 ppm of quinone methide ester derivative and about 0.10 ppm of TIPA is used, i.e. when QM ester derivative and the tertiary amine are taken in a weight percent ratio of 99.97:0.03, which substantially further reduces to 0.07% when about 300 ppm of quinone methide ester derivative and about 0.5 ppm of TIPA is used, i.e. when QM ester derivative and the tertiary amine are taken in a weight percent ratio of 99.83:0.17, which further substantially reduces to 0% when about 300 ppm of quinone methide ester derivative and about 1 ppm of TIPA is used, i.e. when QM ester derivative and the tertiary amine are taken in a weight percent ratio of 99.67:0.33.

Similar effects have been found when TIPA is replaced with THEED or when TIPA is combined with THEED.

It may be noted that in above embodiments, the polymerization of monomers including styrene has been substantially reduced, which in preferred embodiments has been reduced to less than about 2.0%, in other preferred embodiments has been reduced to less than about 1.5%, and in further preferred embodiments has been reduced to less than about 1.0%, and in still further preferred embodiments has been reduced to about 0% or 0%.

When comparing the results of the present composition with that of compositions consisting of only amine alone, these are far more superior for the present composition, i.e. the present composition is far more substantially improved than the composition consisting of only amine alone.

Therefore, the above findings confirm surprising, unexpected and synergistic effects of the presently provided compositions.

The inventor has found that if the polymerization non-inhibiting amine is selected from one or more of the following tertiary amines, then, surprisingly and unexpectedly, the efficiency of QM derivative does not improve, on the contrary, the polymerization of styrene increases, that is, the inventor has found that the polymerization of styrene, surprisingly and unexpectedly, increases when the tertiary amines of the present invention are replaced with one or more of the amines selected from a group consisting of:
i) N,N,N',N'-Tetrakis(2-hydroxypropyl)ethylene-diamine) Quadrol®;
ii) tetraethylenepentamine (TEPA);
iii) triethanolamine (TEA); and
iv) Tris(N-butylamine) (TBA).

For example, the polymerization of styrene, surprisingly and unexpectedly, increases from about 5.90% when about 100 ppm of quinone methide ester derivative alone is used to about 6.10% when composition consisting of about 100 ppm of quinone methide ester derivative and about 1 ppm of polymerization non-inhibiting amine, especially Quadrol® is used, and to about 8.38% when composition consisting of about 100 ppm of quinone methide ester derivative and about 1 ppm of polymerization non-inhibiting amine, especially tributylamine (TBA) is used, and to about 8.63% when composition consisting of about 100 ppm of quinone methide ester derivative and about 1 ppm of polymerization non-inhibiting amine, especially triethanol amine (TEA) is used.

Similarly, for example, the polymerization of styrene, surprisingly and unexpectedly, increases from about 0.90% when about 200 ppm of quinone methide ester derivative alone is used to about 1.10% when composition consisting of about 200 ppm of quinone methide ester derivative and about 5 ppm of Quadrol® is used, and increases to about 1.25% when composition consisting of about 200 ppm of quinone methide ester derivative and about 5 ppm of TBA is used, and increases to about 1.32% when composition consisting of about 200 ppm of quinone methide ester derivative and about 5 ppm of TEA is used.

The inventor has further found that the polymerization of styrene, surprisingly and unexpectedly, increases when the tertiary amines of the present invention are replaced with one or more of nitroxide compound including 1-oxyl-2,2,6,6, tetramethylpiperidin-4-ol (or 4 Hydroxy Tempo or 4-HT).

For example, the polymerization of styrene, surprisingly and unexpectedly, increases from about 5.90% when about 100 ppm of quinone methide ester derivative alone is used to about 6.11% when composition consisting of about 100 ppm of quinone methide ester derivative and about 5 ppm of 4HT is used, and increases from about 1.99% when about 150 ppm of quinone methide ester derivative alone is used to about 2.70% when composition consisting of about 150 ppm of quinone methide ester derivative and about 5 ppm of 4HT is used, and increases from about 0.90% when about 200 ppm of quinone methide ester derivative alone is used to about 1.21% when composition consisting of about 200 ppm of quinone methide ester derivative and about 5 ppm of 4HT is used.

The inventor has further found that the polymerization of styrene, surprisingly and unexpectedly, increases even when composition consisting of quinone methide derivative and of TEPA is used.

Therefore, in accordance with one of the embodiments of the present invention, the Quadrol®, TEPA, TBA, TEA, and 4HT are excluded from scope of the present invention.

Therefore, in accordance with one of the embodiments of the present invention, the additive composition of the present invention does not comprise one or more of following amines:
i) N,N,N',N'-Tetrakis(2-hydroxypropyl)ethylene-diamine) Quadrol®;
ii) tetraethylenepentamine (TEPA);
iii) triethanolamine (TEA); and
iv) Tris(N-butylamine) (TBA).

Furthermore, in accordance with one of the embodiments of the present invention, the additive composition of the present invention does not comprise nitroxide (i.e. nitroxyl) compounds including 1-oxyl-2,2,6,6, tetramethylpiperidin-4-ol (or 4 Hydroxy Tempo or 4-HT).

However, as it can be observed, the comparison of the polymerization efficiency with the tertiary amines of the present invention confirms the surprising, unexpected and synergistic effects of the presently provided compositions.

It may be noted that as per the present invention, the QM derivatives may be prepared by any conventionally known method. For example, the QM derivatives, particularly the QM ester derivative may be prepared by a method disclosed in U.S. Pat. No. 5,583,247.

In one embodiment of the present invention, the additive compositions of the present invention may be used in an amount which is selected from the group comprising the amount varying from:
 a. about 0.01 to about 2000 ppm,
 b. about 1 to about 1200 ppm,
 c. about 5 to about 1000 ppm,
 d. about 50 to about 500 ppm, and
 e. about 100 to about 300 ppm, and
 which is added to the aromatic vinyl monomers stream based on weight of the monomer.

In one embodiment, the present invention relates to a method of preparation of the above-described additive composition of the present invention for controlling and inhibiting polymerization of monomers including styrene, wherein the additive composition consisting of one or more of the quinone methide derivatives and one or more of the tertiary amines is prepared by mixing one or more of the quinone methide derivatives and one or more of the tertiary amines of the present invention.

Accordingly, in one of the embodiments, the present invention relates to a method of preparation of the additive composition of the present invention for controlling and inhibiting polymerization of aromatic vinyl monomers including styrene, wherein the method comprises mixing one or more of the quinone methide derivatives and one or more of the tertiary amines of the present invention.

In accordance with one of the preferred embodiments of the present invention, the quinone methide derivatives and the tertiary amines are mixed in a weight percent ratio selected from the group comprising the weight percent ratio of quinone methide derivative:tertiary amine varying from
i. about 99.99:0.01 to about 40:60,
ii. about 99.9:0.1 to about 50:50,
iii. about 99:1 to about 60:40,
iv. about 95:5 to about 70:30, and
v. about 90:10 to about 85:15.

In accordance with one of the preferred embodiments of the present invention, the quinone methide derivatives and the tertiary amines may be mixed directly, or after dissolving in a solvent, wherein the solvent is capable of dissolving the derivatives and the amines.

In another embodiment, the present invention relates to use of or a method of using above-described additive compositions of the present invention to control and inhibit polymerization of monomers including styrene, wherein the additive composition consists of one or more of the quinone methide derivatives and one or more of the tertiary amines of the present invention.

In accordance with the present invention, the additive compositions of the present invention may be used after mixing its components, i.e. as pre-blended composition or each ingredient of the composition may be added separately to the processing unit of styrene.

Accordingly, in one of the embodiments, the present invention also relates to use of or a method of using the additive compositions of the present invention for control and inhibition of polymerization of aromatic vinyl monomers including styrene, wherein the method comprises adding the additive composition of the present invention to a processing or manufacturing unit for styrene polymerization, wherein the additive composition consists of mixture of one or more of the quinone methide derivatives and one or more of the tertiary amines of the present invention.

Accordingly, in one embodiment, the present invention also relates to use of or a method of using the above-described additive compositions of the present invention for control and inhibition of polymerization of aromatic vinyl monomers including styrene, wherein the method comprises separately adding components of the additive composition of the present invention to a processing or manufacturing unit for styrene polymerization, wherein the additive composition consists of component a) one or more of the quinone methide derivatives and component b) one or more of the said tertiary amines of the present invention.

It may be added continuously to satisfy requirement of continuous flow of styrene in the processing or manufacturing unit. It may be added directly to the processing or manufacturing unit, or after dissolving in a suitable solvent or diluent which may include aromatic solvent or diluent. It may be added either in the beginning of process or when the manufacturing process has started.

In accordance with one of the preferred embodiments of the present invention, the quinone methide derivatives and the tertiary amines are added to the processing or manufacturing unit for styrene polymerization in a weight percent ratio selected from the group comprising the weight percent ratio of
quinone methide derivative:tertiary amine varying from
i. about 99.99:0.01 to about 40:60,
ii. about 99.9:0.1 to about 50:50,
iii. about 99:1 to about 60:40,
iv. about 95:5 to about 70:30, and
v. about 90:10 to about 85:15.

In accordance with one of the embodiments of the present invention, the present compositions may be added in one of the following amounts selected from the group comprising:
 a. varying from about 0.01 to about 2000 ppm,
 b. varying from about 1 to about 1200 ppm,
 c. varying from about 5 to about 1000 ppm,
 d. varying from about 50 to about 500 ppm, and
 e. varying from about 100 to about 300 ppm,
 to the aromatic vinyl monomers stream in the processing or manufacturing unit for styrene polymerization based on weight of the monomers.

In accordance with one of the preferred embodiments of the present invention, the quinone methide derivatives and the tertiary amines are added either separately or after mixing with each other.

In accordance with one of the preferred embodiments of the present invention, the quinone methide derivatives and the tertiary amines may also be added after mixing with a solvent which is capable of dissolving the derivatives and the amines.

In one of the embodiments, the present invention also relates to a method for controlling and inhibition of polymerization of aromatic vinyl monomers including styrene by adding the additive composition of the present invention to the monomer, or monomer stream, or monomers, or monomer stream, wherein the composition may be added in an amount as defined herein.

Accordingly, in one of the embodiments, the present invention relates to a method for controlling and inhibition of polymerization of aromatic vinyl monomers including styrene, wherein the method comprises adding the additive composition of the present invention to a processing or manufacturing unit for styrene polymerization, wherein the additive composition consists of one or more of the quinone methide derivatives and one or more of the tertiary amines of the present invention.

In accordance with one of the preferred embodiments of the present invention, the quinone methide derivatives and the tertiary amines are added in a weight percent ratio selected from the group comprising the weight percent ratio of quinone methide derivative:tertiary amine varying from
i. about 99.99:0.01 to about 40:60,
ii. about 99.9:0.1 to about 50:50,
iii. about 99:1 to about 60:40,
iv. about 95:5 to about 70:30, and
v. about 90:10 to about 85:15.

In accordance with one of the preferred embodiments of the present invention, the quinone methide derivatives and the tertiary amines are added either separately or after mixing with each other.

In accordance with one of the preferred embodiments of the present invention, the quinone methide derivatives and the tertiary amines may also be added after mixing with a solvent which is capable of dissolving the derivatives and the amines.

In accordance with one of the preferred embodiments of the present invention, the composition consisting of one or more of the quinone methide derivatives and one or more of the tertiary amines is added to the aromatic vinyl monomers stream in the processing or manufacturing unit for styrene polymerization based on weight of the monomers in an amount selected from the group comprising:
a. varying from about 0.01 to about 2000 ppm,
b. varying from about 1 to about 1200 ppm,
c. varying from about 5 to about 1000 ppm,
d. varying from about 50 to about 500 ppm, and
e. varying from about 100 to about 300 ppm.

In accordance with one of the preferred embodiments of the present invention, the additive compositions of the present invention or as prepared by the method of the present invention may be used or employed at a temperature range which is selected from the group comprising the temperature varying from about 60° C. to about 180° C., and from about 90° C. to about 140° C.

In accordance with one of the preferred embodiments of the present invention, in the methods of the present invention as described herein, the monomers are in a processing stage.

In accordance with one of the preferred embodiments of the present invention, in the methods of the present invention as described herein, the monomers are at a temperature varying from about 60° C. to about 180° C.

In accordance with one of the preferred embodiments of the present invention, in the methods of the present invention as described herein, the monomers are in a manufacturing stage.

It may be noted that the expression "are taken in percent ratio varying from about 99:1 to about 50:50" and so on are intended to include the ratio of 99:1 and 50:50, and so on.

It may also be noted that "in percent ratio" means "in weight percent ratio" or "in percent ratio by weight" unless specifically otherwise provided.

EXAMPLES

The present invention is now described with the help of following examples, which are not intended to limit scope of the present invention.

Experiment 10 g distilled styrene and required amount of the amine are taken in a reactor (equivalent to processing or manufacturing unit of styrene polymerization, which for the laboratory experiments may be as a tube) equipped with thermometer and nitrogen inlet and outlet. Enough continuous $N_2$ flow varying from about 10-15 ml/min is maintained to ensure proper agitation. The contents of the reactor are heated to about 120° C. under continuous nitrogen flow for 2 h. After 2 h, the reactor is cooled to below 10° C. by immersing in crushed ice. The contents of the reactor are then poured into a beaker containing methanol. The precipitate obtained is filtered, dried to remove methanol and weighed. Approximately, for 1.5-2 g chilled polymerization, 80 g methanol was used to precipitate the polymer formed in the styrene solution. The weight of the precipitate is reported as % polymer formed in below Tables. The styrene was distilled and purified before use to remove the stabilizers.

Examples

Blank and with Prior Art Additive—Quinone Methide

The above experiment without additive is carried out to get the blank reading.

The above experiment with prior art additive—quinone methide (4-benzylidene, 2,6 di-tert-butyl-cyclohexa-2,5 dienone) (QM) is carried for active dosages of 100 ppm, and 150 ppm for QM and for comparison purpose.

TABLE 1

| Example No. | Additive | Active Dosage (ppm) | % Polymerization |
|---|---|---|---|
| 1 | Blank | — | 19.66 |
| 2 | Quinone Methide (QM) | 100 | 9.6 |
| 3 | Quinone Methide (QM) | 150 | 7.24 |

It can be seen from the above Table 1 that with said prior art additive quinone methide for the dosage of about 150 ppm, the polymerization of styrene is substantially high of about 7.24%, and for the dosage of about 100 ppm, the polymerization of styrene is substantially further high of about 9.6%. Therefore, it is observed that quinone methide is not suitable at lower dosages.

Examples with Amines Per Se of the Present Compositions and the Comparative Amines:

The above experiment with amines per se is carried out at 200 ppm to know whether these amines per se are capable of inhibiting the polymerization of styrene or not, and data is given in Table 2.

TABLE 2

| Example No. | Additive | Active Dosage (ppm) | % Polymerization |
|---|---|---|---|
| 4 | TIPA [from Sterling] | 200 | 17.08 |
| 5 | TIPA [from DOW] | 200 | 16.16 |
| 6 | THEED | 200 | 17.8 |
| 7 | Quadrol ® | 200 | 14.64 |
| 8 | TEA | 200 | 16.9 |
| 9 | TBA | 200 | 16.21 |
| 10 | DEA | 200 | 15.27 |
| 11 | MEA | 200 | 15.47 |
| 12 | UOP5 | 200 | 17.80 |

It can be seen from the above Table 2 that all amines per se including the amines of the present compositions—TIPA and THEED and the comparative amines at a dosage of about 200 ppm result in polymerization of styrene to the extent varying from about 14.64% to 17.80%, which on comparison with data of blank experiment confirms that amines per se are not capable of inhibiting the polymerization of styrene, and therefore, the amines have been named as "polymerization non-inhibitors amines".

Examples

Blank and with Prior Art Additive—Quinone Methide Ester Derivative

The above experiment without additive is carried out to get the blank reading.

The above experiment with prior art additive—quinone methide ester derivative is carried for active dosages of 100 and 150 ppm for comparison purpose.

TABLE 3

| Example No. | Additive | Active Dosage (ppm) | % Polymerization |
|---|---|---|---|
| 1 | Blank | — | 19.66 |
| 13a | Quinone methide ester (purity 95% by HPLC | 100 | 5.90* |
| 13b | Quinone methide ester (purity 95% by HPLC | 150 | 1.99* |

*It may be noted that we have corrected the typographical error in above table to correct the value of 5.89 as 5.90, and 1.59 as 1.99.

Examples with Present Composition Vis-à-Vis Prior Art or Comparative Compositions The above experiment was carried out with compositions of the present invention consisting of quinone methide ester derivative and tertiary amines (TIPA and THEED) to know the inhibition capability of compositions of the present invention and data has been compared with the prior art or comparative additives.

TABLE 4

| Example No. | Additive | Active Dosage (ppm) | % Polymerization |
|---|---|---|---|
| 14 | QM Ester + TIPA | 100 + 1 | 4.3* |
| 15. | QM Ester + TIPA | 150 + 0.75 | 0.89* |
| 16. | QM Ester + Quadrol ® | 100 + 1 | 6.10 |

TABLE 4-continued

| Example No. | Additive | Active Dosage (ppm) | % Polymerization |
|---|---|---|---|
| 17. | QM Ester + Tributyl amine (TBA) | 100 + 1 | 8.38 |
| 18 | QM Ester + Triethanol amine (TEA) | 100 + 1 | 8.63 |

*It may be noted that we have corrected the typographical error in above table to correct the value of 0.33 as 0.89.

TABLE 5

| Example No. | Additive (combination of QM ester + TIPA) in active dosage (ppm) | % Polymerization |
|---|---|---|
| 14 | 100 + 1 | 4.3 |
| 19 | 100 + 2 | 3.91 |
| 20 | 100 + 3 | 3.68 |
| 21 | 100 + 4 | 3.50 |
| 22 | 100 + 5 | 3.35 |
| 23 | 100 + 10 | 2.90 |
| 24 | 100 + 15 | 2.51 |
| 25 | 100 + 20 | 2.30 |
| 26 | 100 + 30 | 1.90 |
| 27 | 100 + 40 | 1.55 |
| 28 | 100 + 100 | 1.46 |

TABLE 6

| Example No. | Additive (combination of QM ester + THEED) in active dosage (ppm) | % Polymerization |
|---|---|---|
| 29 | 100 + 1 | 4.99 |
| 30 | 100 + 10 | 3.79 |
| 31 | 100 + 15 | 3.31 |
| 32 | 100 + 20 | 3.10 |
| 33 | 100 + 30 | 2.85 |
| 34 | 100 + 40 | 2.45 |

TABLE 7

| Example No. | Additive (combination of QM ester + 4HT) in active dosage (ppm) | % Polymerization |
|---|---|---|
| 35 | 100 + 5 | 6.11 |
| 36 | 100 + 10 | 6.16 |
| 37 | 100 + 15 | 6.08 |
| 38 | 100 + 20 | 6.21 |
| 39 | 100 + 30 | 6.25 |
| 40 | 100 + 40 | 6.28 |

TABLE 8

| Example No. | Additive (combination of QM ester + TIPA) in active dosage (ppm) | % Polymerization |
|---|---|---|
| 41 | 150 + 0.1 | 1.65 |
| 42 | 150 + 0.5 | 1.32 |
| 15 | 150 + 0.75 | 0.89 |
| 43 | 150 + 1.0 | 0.82 |
| 44 | 150 + 1.5 | 0.75 |
| 45 | 150 + 3.0 | 0.66 |
| 46 | 150 + 4.5 | 0.51 |
| 47 | 150 + 6.0 | 0.40 |
| 48 | 150 + 10 | 0.35 |
| 49 | 150 + 20 | 0.28 |
| 50 | 150 + 30 | 0.25 |

TABLE 8-continued

| Example No. | Additive (combination of QM ester + TIPA) in active dosage (ppm) | % Polymerization |
|---|---|---|
| 51 | 150 + 40 | 0.20 |
| 52 | 150 + 150 | 0.08 |

TABLE 9

| Example No. | Additive (combination of QM ester + THEED) in active dosage (ppm) | % Polymerization |
|---|---|---|
| 53 | 150 + 10 | 1.52 |
| 54 | 150 + 20 | 1.42 |
| 55 | 150 + 30 | 1.27 |
| 56 | 150 + 40 | 1.19 |

TABLE 10

| Example No. | Additive (combination of QM ester + 4HT) in active dosage (ppm) | % Polymerization |
|---|---|---|
| 57 | 150 + 5 | 2.70 |
| 58 | 150 + 10 | 2.80 |
| 59 | 150 + 20 | 2.75 |
| 60 | 150 + 30 | 2.79 |
| 61 | 150 + 40 | 2.69 |

TABLE 11

| Example No. | Additive (combination of QM ester + TIPA) in active dosage (ppm) | % Polymerization |
|---|---|---|
| 62 | 200 + 0.1 | 0.78 |
| 63 | 200 + 0.5 | 0.55 |
| 64 | 200 + 1 | 0.40 |
| 65 | 200 + 5 | 0.25 |
| 66 | 200 + 10 | 0.21 |
| 67 | 200 + 15 | 0.19 |
| 68 | 200 + 20 | 0.12 |
| 69 | 200 + 30 | 0.07 |
| 70 | 200 + 40 | 0 |

TABLE 12

| Example No. | Additive (combination of QM ester + THEED) in active dosage (ppm) | % Polymerization |
|---|---|---|
| 71 | 200 + 1 | 0.78 |
| 72 | 200 + 5 | 0.62 |
| 73 | 200 + 10 | 0.57 |
| 74 | 200 + 15 | 0.55 |
| 75 | 200 + 20 | 0.49 |
| 76 | 200 + 30 | 0.47 |
| 77 | 200 + 40 | 0.39 |

TABLE 13

| Example No. | Additive (combination of QM ester + 4HT) in active dosage (ppm) | % Polymerization |
|---|---|---|
| 78 | 200 + 5 | 1.21 |
| 79 | 200 + 10 | 1.27 |
| 80 | 200 + 15 | 1.24 |
| 81 | 200 + 20 | 1.32 |
| 82 | 200 + 30 | 1.33 |
| 83 | 200 + 40 | 1.36 |

TABLE 14

| Example No. | Additive (combination of QM ester + Quadrol ®) in active dosage (ppm) | % Polymerization |
|---|---|---|
| 84 | 200 + 5 | 1.10 |
| 85 | 200 + 10 | 1.08 |
| 86 | 200 + 15 | 1.08 |
| 87 | 200 + 20 | 1.05 |
| 88 | 200 + 30 | 1.10 |
| 89 | 200 + 40 | 1.05 |

TABLE 15

| Example No. | Additive (combination of QM ester + TBA) in active dosage (ppm) | % Polymerization |
|---|---|---|
| 90 | 200 + 5 | 1.25 |
| 91 | 200 + 10 | 1.27 |
| 92 | 200 + 15 | 1.30 |

TABLE 16

| Example No. | Additive (combination of QM ester + TEA) in active dosage (ppm) | % Polymerization |
|---|---|---|
| 93 | 200 + 5 | 1.32 |
| 94 | 200 + 10 | 1.39 |
| 95 | 200 + 15 | 1.42 |

TABLE 17

| Example No. | Additive (combination of QM ester + TIPA) in active dosage (ppm) | % Polymerization |
|---|---|---|
| 96 | 300 + 0.1 | 0.15 |
| 97 | 300 + 0.5 | 0.07 |
| 98 | 300 + 1 | 0 |
| 99 | 300 + 5 | 0 |
| 100 | 300 + 10 | 0 |

TABLE 18

| Example No. | Additive (combination of QM ester + THEED) in active dosage (ppm) | % Polymerization |
|---|---|---|
| 101 | 300 + 0.1 | 0.20 |
| 102 | 300 + 0.5 | 0.15 |
| 103 | 300 + 1 | 0.12 |
| 104 | 300 + 5 | 0.10 |
| 105 | 300 + 10 | 0.08 |

The above experimental findings confirm surprising, unexpected and synergistic effects of the presently provided compositions.

The above findings also confirm that compositions of present invention have technical advantages and surprising effects over the prior art and comparative additives and compositions.

It may also be noted that the term "about" is not intended to enlarge scope of the range defined herein, but is intended to include the experimental errors permissible in the field of the invention.

The invention claimed is:

1. Additive composition for controlling and inhibition of polymerization of aromatic vinyl monomers including styrene consisting of:
   (a) one or more of quinone methide derivatives; and
   CHARACTERIZED IN THAT the composition further comprises:
   (b) one or more of tertiary amines,
   wherein said tertiary amine is selected from a group consisting of:
   (i) tri isopropanol amine (TIPA),
   (ii) N,N,N',N'-Tetrakis (2-hydroxyethyl)ethylene-diamine (THEED), and
   (iii) mixture thereof.

2. The additive composition as claimed in claim 1, wherein the quinone methide derivative is selected from a group comprising:
   i) alkyl-(3,5-di-tert-butyl-4-oxocyclohexane-2,5-dienylidene)-cyano derivative of quinone methide;
   ii) alkyl-(3,5-di-tert-butyl-4-oxocyclohexane-2,5-dienylidene)-acid derivative of quinone methide;
   iii) alkyl-(3,5-di-tert-butyl-4-oxocyclohexane-2,5-dienylidene)-ester derivative of quinone methide; and
   iv) combination thereof.

3. The additive composition as claimed in claim 1, wherein the quinone methide derivative is alkyl-(3,5-di-tert-butyl-4-oxocyclohexane-2,5-dienylidene)-ester derivative of quinone methide.

4. The additive composition as claimed in claim 2, wherein the alkyl group is selected from a group comprising methyl-group, ethyl-group and propyl-group.

5. The additive composition as claimed in claim 1, wherein the quinone methide derivative does not include 7-aryl quinone methide derivatives.

6. The additive composition as claimed in claim 1, wherein the composition does not comprise one or more of following compounds selected from the group comprising:
   i) N,N,N',N'-Tetrakis (2-hydroxypropyl)ethylene-diamine Quadrol®;
   ii) tetraethylenepentamine (TEPA);
   iii) triethanolamine (TEA);
   iv) Tris(N-butylamine) (TBA);
   v) ethylene diamine (EDA); and
   vi) nitroxide (i.e. nitroxyl) compound including 1-oxyl-2, 2,6,6, tetramethylpiperidin-4-ol (or 4 Hydroxy Tempo or 4-HT).

7. The additive composition as claimed in claim 1, wherein the quinone methide derivative and the tertiary amine are present in a weight percent ratio, wherein the weight percent ratio is selected from the group comprising the weight percent ratio of quinone methide derivative:tertiary amine varying from:
   i. about 99.99:0.01 to about 40:60,
   ii. about 99.9:0.1 to about 50:50,
   iii. about 99:1 to about 60:40,
   iv. about 95:5 to about 70:30, and
   v. about 90:10 to about 85:15.

8. The additive composition as claimed in claim 1, wherein the composition is used in an amount which is selected from the group comprising the amount varying from:
   a. about 0.01 to about 2000 ppm,
   b. about 1 to about 1200 ppm,
   c. about 5 to about 1000 ppm,
   d. about 50 to about 500 ppm, and
   e. about 100 to about 300 ppm, and
   is added to the aromatic vinyl monomers stream based on weight of the monomer.

9. A method of preparation of the additive composition for control and inhibition of polymerization of aromatic vinyl monomers including styrene as claimed in claim 1, wherein the method comprises mixing one or more of the quinone methide derivatives and one or more of the tertiary amines.

10. The method as claimed in claim 9, wherein the quinone methide derivatives and the tertiary amines are mixed in a weight percent ratio selected from the group comprising the weight percent ratio of quinone methide derivative:tertiary amine varying from
    i. about 99.99:0.01 to about 40:60,
    ii. about 99.9:0.1 to about 50:50,
    iii. about 99:1 to about 60:40,
    iv. about 95:5 to about 70:30, and
    v. about 90:10 to about 85:15.

11. A method of using the additive composition of claim 1 for control and inhibition of polymerization of aromatic vinyl monomers including styrene, wherein the method comprises adding the additive composition to a processing or manufacturing unit for styrene polymerization, wherein the additive composition consists of one or more of the quinone methide derivatives and one or more of the tertiary amines.

12. The method as claimed in claim 11, wherein the quinone methide derivatives and the tertiary amines are added to the processing or manufacturing unit for styrene polymerization in a weight percent ratio selected from the group comprising the weight percent ratio of quinone methide derivative:tertiary amine varying from
    i. about 99.99:0.01 to about 40:60,
    ii. about 99.9:0.1 to about 50:50,
    iii. about 99:1 to about 60:40,
    iv. about 95:5 to about 70:30, and
    v. about 90:10 to about 85:15.

13. The method as claimed in claim 11, wherein the composition is added in an amount selected from the group comprising:
    a. varying from about 0.01 to about 2000 ppm,
    b. varying from about 1 to about 1200 ppm,
    c. varying from about 5 to about 1000 ppm,
    d. varying from about 50 to about 500 ppm, and
    e. varying from about 100 to about 300 ppm,
    to the aromatic vinyl monomers stream in the processing or manufacturing unit for styrene polymerization based on weight of the monomers.

14. The method as claimed in claim 11, wherein the quinone methide derivatives and the tertiary amines are added either separately or after mixing with each other.

15. The method as claimed in claim 11, wherein the quinone methide derivatives and the tertiary amines are added after mixing with a solvent which dissolves the derivatives and the amines.

16. A method for controlling and inhibition of polymerization of aromatic vinyl monomers including styrene, wherein the method comprises adding the additive composition of claim 1 to a processing or manufacturing unit for styrene polymerization, wherein the additive composition consists of one or more of the quinone methide derivatives and one or more of the tertiary amines.

17. The method as claimed in claim 16, wherein the quinone methide derivatives and the tertiary amines are added in a weight percent ratio selected from the group comprising the weight percent ratio of quinone methide derivative:tertiary amine varying from
i. about 99.99:0.01 to about 40:60,
ii. about 99.9:0.1 to about 50:50,
iii. about 99:1 to about 60:40,
iv. about 95:5 to about 70:30, and
v. about 90:10 to about 85:15.

18. The method as claimed in claim 16, wherein the additive composition is added in an amount selected from the group comprising:
a. varying from about 0.01 to about 2000 ppm,
b. varying from about 1 to about 1200 ppm,
c. varying from about 5 to about 1000 ppm,
d. varying from about 50 to about 500 ppm, and
e. varying from about 100 to about 300 ppm.

19. The method as claimed in claim 16, wherein the quinone methide derivatives and the tertiary amines are added either separately or after mixing with each other.

20. The method as claimed in claim 16, wherein the quinone methide derivatives and the tertiary amines are added after mixing with a solvent which dissolves the derivatives and the amines.

21. The method as claimed in claim 11, wherein said composition is used at a temperature range which is selected from the group comprising the temperature varying from about 60° C. to about 180° C., and from about 90° C. to about 140° C.

22. The method as claimed in claim 11, wherein said monomers are in a processing stage or in a manufacturing stage.

23. The method as claimed in claim 11, wherein said monomers are at a temperature varying from about 60° C. to about 180° C.

* * * * *